United States Patent
Goroshevskiy et al.

(10) Patent No.: US 10,330,641 B2
(45) Date of Patent: Jun. 25, 2019

(54) METALLIC CONSTRUCTIONS MONITORING AND ASSESSMENT IN UNSTABLE ZONES OF THE EARTH'S CRUST

(71) Applicants: Valerian Goroshevskiy, Moscow (RU); Svetlana Kamaeva, Moscow (RU); Igor Kolesnikov, Moscow (RU); Leonid Ivlev, Moscow (RU)

(72) Inventors: Valerian Goroshevskiy, Moscow (RU); Svetlana Kamaeva, Moscow (RU); Igor Kolesnikov, Moscow (RU); Leonid Ivlev, Moscow (RU)

(*) Notice: Subject to any disclaimer, the term of this patent is extended or adjusted under 35 U.S.C. 154(b) by 57 days.

(21) Appl. No.: 15/652,398

(22) Filed: Jul. 18, 2017

(65) Prior Publication Data
US 2017/0350864 A1 Dec. 7, 2017

Related U.S. Application Data

(63) Continuation-in-part of application No. 15/403,476, filed on Jan. 11, 2017, now Pat. No. 9,964,519, which is a continuation-in-part of application No. 14/867,538, filed on Sep. 28, 2015, now Pat. No. 9,581,567, which is a continuation-in-part of
(Continued)

(51) Int. Cl.
| | |
|---|---|
| *G01N 27/82* | (2006.01) |
| *B64C 39/02* | (2006.01) |
| *G01M 5/00* | (2006.01) |
| *G01L 1/12* | (2006.01) |

(Continued)

(52) U.S. Cl.
CPC .......... *G01N 27/82* (2013.01); *B64C 39/024* (2013.01); *G01L 1/125* (2013.01); *G01M 5/0008* (2013.01); *G01M 5/0025* (2013.01); *G01M 5/0033* (2013.01); *G01M 5/0058* (2013.01); *G01V 3/08* (2013.01); *B64C 2201/123* (2013.01); *G01B 7/24* (2013.01); *G01B 2210/58* (2013.01)

(58) Field of Classification Search
CPC ..... G01N 27/82; G01B 2210/58; G01M 5/25; G01M 5/58; G01M 5/33; G01M 5/08
See application file for complete search history.

(56) References Cited

U.S. PATENT DOCUMENTS

| | | | | |
|---|---|---|---|---|
| 4,847,557 A | * | 7/1989 | Saito | ........... G01P 1/026 |
| | | | | 324/207.13 |
| 5,336,998 A | * | 8/1994 | Watts | .......... G01N 27/82 |
| | | | | 324/235 |

(Continued)

*Primary Examiner* — Tung X Nguyen
*Assistant Examiner* — Dominic E Hawkins
(74) *Attorney, Agent, or Firm* — Nadya Reingand; Yan Hankin

(57) ABSTRACT

A method for discovering, identifying, and monitoring of mechanical defects in a ferromagnetic underground or underwater structure. A magnetic scanner portable device is used to inspect the ferromagnetic underground structure and identify at least one portion with a magnetic field anomaly. Sets of permanent magnetic scanner sensors to monitor the magnetic field anomaly are placed adjacent to the at least one portion of the underground structure. A calculation unit, coupled to the sets of permanent magnetic scanner sensors is used to collect and process data. A stress-deformed state (SDS) and a risk-factor (RF) of the at least one portion with the magnetic field anomaly is presented on a display unit, which is coupled to the calculation unit.

13 Claims, 8 Drawing Sheets

Related U.S. Application Data application No. 14/551,295, filed on Nov. 24, 2014, now Pat. No. 9,746,444, which is a continuation-in-part of application No. 13/920,216, filed on Jun. 18, 2013, now Pat. No. 9,176,096, which is a continuation-in-part of application No. 13/674,118, filed on Nov. 12, 2012, now Pat. No. 8,542,127, which is a continuation-in-part of application No. 13/662,427, filed on Oct. 27, 2012, now Pat. No. 8,447,532.

(51) Int. Cl.
*G01V 3/08* (2006.01)
*G01B 7/24* (2006.01)

(56) References Cited

U.S. PATENT DOCUMENTS

| | | | | |
|---|---|---|---|---|
| 5,532,589 A * | 7/1996 | Gammell | ............ | G01N 27/825 324/226 |
| 5,534,775 A * | 7/1996 | Lam | ............ | G01N 27/84 324/216 |
| 6,239,593 B1 * | 5/2001 | Burkhardt | ............ | G01B 7/24 324/209 |
| 8,841,901 B2 * | 9/2014 | Goroshevskiy | ............ | G01S 19/49 324/228 |
| 2007/0247145 A1 * | 10/2007 | Zimmermann | ............ | G01N 27/87 324/242 |
| 2010/0089126 A1 * | 4/2010 | Sweeney | ............ | B63C 11/42 73/40 |
| 2010/0163433 A1 * | 7/2010 | Horn | ............ | G01N 27/20 205/790.5 |
| 2012/0103245 A1 * | 5/2012 | Lambertus | ............ | B63C 11/42 114/331 |
| 2012/0256634 A1 * | 10/2012 | Morys | ............ | E21B 43/2401 324/338 |
| 2012/0262708 A1 * | 10/2012 | Connolly | ............ | B64C 39/024 356/237.2 |
| 2013/0006543 A1 * | 1/2013 | Hiwatashi | ............ | G01M 5/0033 702/42 |

\* cited by examiner

| G/1 | G/2 | Y/3 | G/4 | G/5 | G/6 | G/7 | Y/8 |
|---|---|---|---|---|---|---|---|
| G/9 | G/10 | G/11 | G/12 | G/13 | G/14 | G/15 | G/16 |
| Y/17 | G/18 | G/19 | G/20 | G/21 | G/22 | R/23 | G/24 |
| G/25 | G/26 | G/27 | G/28 | G/29 | G/30 | G/31 | G/32 |
| G/33 | G/34 | G/35 | Y/36 | G/35 | | | |

Area №3
Condition:
Y

Details

Critical Areas

METALLIC CONSTRUCTIONS MONITORING AND ASSESSMENT IN UNSTABLE ZONES OF THE EARTH'S CRUST

CROSS-REFERENCE TO RELATED APPLICATION

This application is a Continuation-in-Part of U.S. patent application Ser. No. 15/403,476, filed Jan. 11, 2017, which is a Continuation-in-Part of U.S. patent application Ser. No. 14/867,538, filed Sep. 28, 2015, now U.S. Pat. No. 9,581,567, which is a Continuation-in-Part of U.S. patent application Ser. No. 14/551,295, filed Nov. 24, 2014, now allowed, which is a Continuation-in-Part of U.S. patent application Ser. No. 13/920,216, filed Jun. 18, 2013, now U.S. Pat. No. 9,176,096, which is a Continuation-in-Part of U.S. patent application Ser. No. 13/674,118, filed Nov. 12, 2012, now U.S. Pat. No. 8,542,127, which is a Continuation-in-Part of U.S. patent application Ser. No. 13/662,427, filed Oct. 27, 2012, now U.S. Pat. No. 8,447,532. This application claims priority to, and incorporates fully by reference, each said Patent Application as well as U.S. Provisional Patent Application No. 61/807,378, filed Apr. 2, 2013.

FIELD OF INVENTION

The present invention relates broadly to a method and a device for continuous (extended) ferromagnetic structures inspection and monitoring in earthquake zones for possible mechanical defects, and particularly to magnetic scanner methods and devices, using magnetic tomography for real-time structural defects measurement and assessment.

BACKGROUND OF THE INVENTION

This invention can be used in various fields where constructions are tested for continuity defects in a contact fashion or combined with the remote method. Examples of device and method implementation may include pipes for oil and gas industry, detection of flaws in rolled products in metallurgical industry, welding quality of heavy duty equipment such as ships and reservoirs, etc. It is especially important for inspection of loaded constructions, such as pressured pipes, infrastructure maintenance, nuclear power plant monitoring, bridges, corrosion prevention, and environment protection.

Similar to modes of transportation like roads, railroads, and electric transmission lines, pipelines have an important role in the nation's economy, belonging to the long linear assets. They typically cross large distances from the points of production and import facilities to the points of consumption. Like the other modes of transportation, pipelines require a very large initial investment to be built, having long exploitation periods when properly maintained. Like any engineering structure, pipelines do occasionally fail. While pipeline rates have little impact on the price of a fuel, its disruptions or lack of capacity can constrain supply, potentially causing very large price spikes. This is why pipelines, such as those used in the oil and gas industry, require regular inspection and maintenance before potentially costly failures occur.

Traditional contact methods of assessing the structural integrity typically are complemented by flaw detection using in-line inspection (ILI), detecting and evaluating various metal defects organized by area (clusters), assessing their danger by calculating a level of stress-deformed state (SDS), and deciding on a permissible operating pressure with evaluated factor of repair (EFR), based on residual pipe wall thickness (for defects of "metal loss"—corrosion type).

As a contact technique, pigging devices have been used for many years to maintain larger diameter pipelines in the oil industry. Today, however, the use of smaller diameter pigging devices is increasing in many plants as plant operators search for increased efficiencies and reduced costs. Unfortunately, the ILI using intelligent pigging is unavailable for a wide range objects that require full disruptive inspection and significant spending on repair preparation. While the ILI method is suitable for the initial flaw detection, it is less efficient for the relative degree (ranking) of the risk-factor evaluation, as well as for defective pipeline serviceability calculation.

Pipeline pigging devices can detect the following types of defects: i) changing in geometry: dents, wavy surface, deformed shape of cross-section; ii) metal loss, having mechanical, technological or corrosion nature; material discontinuity: layering and inclusions; iii) cracks; iv) all types of welding defects.

Pipeline pigging is a very expensive and labor-consuming method. The major limitation of this method is the fact that a large part of pipelines are not prepared for pigging device operation, e.g., due to lack of input/output chambers for pig-flow device launching and pipeline cleaning access, partially blocked pipe cross-sections due to welding artifacts, geometrical abnormalities, and large slopes (small radius turns) of the pipeline layout. In order to make the pipeline pigging method possible, a significant preparation has to be done in advance, in particular, the high residual level magnetization (saturated magnetic fields) of the pipeline has to be performed before using the pig-flow device. This causes future technical problems of pipeline demagnetization that become necessary for actual pipe repair after the pigging.

Moreover, the evaluation of the absolute values of mechanical flaws by pigging devices is particularly difficult due to multiple additional factors that have to be taken into account, e.g., bearing capacity of the soil and local cyclical loads (e.g., temperature, etc.).

Aside of the remote methods, there are numerous contact non-destructive testing devices for access to the surface of the metallic construction (ultrasound, eddy-current, magnetic-powder-defectoscopy). The main disadvantage of such methods is the time-consuming procedure of surface preparation that reduces the scope of applicability and leads to high costs, as well as low registration sensitivity and selectivity for hidden internal defects identification.

Typically, a pipeline company will have a thorough pipeline safety program that will include a routine for the identification of pipeline defects and review of pipeline integrity. Such a plan should include, but not be limited to: i) a review of previous inspection reports by a third party expert; ii) excavation of sites identified by this review for visual examination of anomalies; iii) repairs as necessary; and iv) addressing factors in the failure of the pipeline and verifying the integrity of the pipeline.

It is important to mention that the pipeline safety program can be only as effective as the interpretation of internal inspection reports.

There are several magnetographic devices that have been disclosed for non-destructive inspection of ferrous materials. In magneto-graphic inspection and defectoscopy, the tested area of the material is placed in proximity to the magnetic medium. The changes of the surface-penetrating magnetic flux, due to the material flows or deviations, can be recorded.

The resulting "magnetogram" of the material can provide the information about the location, size, and type of the defect or abnormality. In general, this information can be converted into the report about the quality of the material. Obtaining the magnetogram (magnetic picture) of the material during the non-destructive inspection process is very challenging and typically requires additional forms of inspection, such as roentgenogram or an X-ray image.

For example, U.S. Pat. No. 4,806,862 (Kozlov) offers a contact method of magnetographic inspection of quality of materials, where a magnetic substance (such as liquid) is applied to be magnetized together with the tested material. According to the invention, the intensity of the magnetizing field is established by the maximum curvature of the surface of a drop of a magnetic fluid applied onto the surface of the material to be inspected, so that the resulting magnetogram can be used to assess the quality of the material.

In another magnetographic disclosure, U.S. Pat. No. 4,930,026 (Kljuev), the flaw sensor for magnetographic quality inspection is disclosed, which includes a flaw detector and a mechanism for driving the magneto-sensitive transducer. During the scanning procedure, the magnetic leakage fluxes penetrate through the surface of the material in places where flaws occur, resulting in a magnetogram of the tested material.

There is another magnetic technique that has been proposed by U.S. Pat. No. 6,205,859 (Kwun) to improve the defect detection with magneto-strictive sensors for piping inspection. The method involves exciting the magneto-strictive sensor transmitter by using a relatively broadband signal instead of a narrow band signal typically used to avoid signal dispersion effects. The amplified detected signal is transformed by a short-time Fourier transform providing the identifiable signal patterns from either defects or known geometric features in the pipe such as welds or junctions.

There is a known contact device with two single-component collinear flux-gate magnetometers have been reported for the contact magnetometric monitoring and defects detection, RU 2062394. This device is characterized by limited applicability due the slow data reception and processing and low sensitivity that makes it impossible to detect minor deviations of stress-strain state (STS) from the background values, which also leads to low resolution threshold and a high false alarm rate.

The defect areas risk-factor criteria and ranking (such as material stress: F-value) is used for planning a required sequence of repair and maintenance steps. Such criteria were developed by comparing a risk-factor calculated using the defect geometry in calibration bore pits with a predicted risk-factor obtained by the remote magneto-metric data (i.e., comprehensive F-value of particular magnetic anomaly).

The deviations of F-value can be classified as follows: X1—for negligible defects (good technical condition of the metal); X2—for defects that require planned repairs (acceptable technical condition); X3—for defects that require immediate repairs (unacceptable, pre-alarm technical condition, alarm).

The absolute values X1-X3 of the F-value (comprehensive value of magnetic field anomaly) should be defined for each particular case, depending upon the following factors: i) Material (e.g. steel) type; ii) Topological location with the local background magnetic fields variation range, iii) Distance to the object (e.g. pipe-line installation depth), iv) General condition of the deformation-related tension within construction under testing, v) etc.

As a result, the only relative changes (variations) of the magnetic field can be evaluated for the given defective segment (relative to the flawless segment), by comparing to its relative F-values. Thus, the very moment of the ultimate stress-limit crossing can be identified for each defective segment during the real operation (i.e., under pressure/loaded) condition. It can be done by monitoring the development of the defects within its F-value interval, namely, starting from the good technical condition X1 up until the yield-strength-limit approaching and material breakdown. It provides a real possibility to predict the defect's speed development, resulting in increased accuracy in priority order definition for upcoming maintenance steps.

The aforementioned techniques are not satisfactory to be used for efficient prediction in defects development timeline and are not capable of providing a real-time alert about the strength-limits approaching, i.e., when probable construction failure is about to occur. The closest remote technology to the disclosed invention is shown in RU 2264617, which describes the Magnetic Tomography (MT) technique. This technique includes a remote magnetic field vectors measurement in Cartesian coordinates with the movement of a measuring device (magnetometer) along the pipeline, the recording of the anomalies of magnetic field (on top of background magnetic field), processing of the data and reporting on found pipeline defects with their localization shown in a resulting magnetogram. The technique provides a good sensitivity, also capable of discovering the following types of defects: i) Changing in geometry: dents, wavy surface, deformed shape of cross-section; ii) Metal loss, having mechanical, technological or corrosion nature; material discontinuity: layering and inclusions; iii) Cracks; iv) Welding flaws, including girth weld defects. Moreover, such a method provides a risk-factor ranking of the discovered pipe-line defects according to a material tension concentration (factor F).

MT determines the comparative degree of danger of defects by a direct quantitative assessment of the stress-deformed condition of the metal. Conventional surveys only measure the geometrical parameters of a defect. Their subsequent calculations to assess the impact of the defect on the safe operation of the pipe do not take into consideration the stress caused by the defect. Therefore, conventional surveys may fail to detect dangerously stressed areas of the pipe or, conversely, classify a defect as one which requires urgent attention when, in reality, the stress level may be low and the defect presents no immediate threat to the operation of the pipe. Since MT directly measures the stress caused by defects it is an inherently more accurate guide to the safe operation of the pipeline than conventional survey methods.

There are several methods for integrity assessment of extended structures (e.g. metallic pipes) that have been proposed in literature. U.S. Pat. No. 4,998,208 (Buhrow, et al.) discloses a piping corrosion monitoring system that calculates the risk-level safety factor producing an inspection schedule. There is another method disclosed in U.S. Pat. No. 6,813,949 (Masaniello, et al.), which addresses a pipeline inspection system having a serviceability acceptance criteria for pipeline anomalies, specifically wrinkles, with an improved method of correlating ultrasonic test data to actual anomaly characteristics.

The main disadvantages of the previous methods are: i) The scope of its application is limited by large-scale linear objects, which are located at a considerable distance from each other, ii) Difficult real-time implementation of the device, iii) It is impossible to identify the location of individual defects, and to visualize and specify the exact position on the internal or external tested surfaces; iv) There is also a lack of visualization of the obtained information in a form of the resulting tomogram where all the locations of the defective segments with associated respective risk factors (absolute mechanical stress values) are shown.

There is a need for developing a combination of contact and remote techniques in order to increase sensitivity, resolution, and visual representation of the stress-related anomalies within the structure, as well as a probability of operation failure (i.e. risk-factor).

SUMMARY OF THE INVENTION

A device for discovering, identification, and monitoring of mechanical defects in an extended metallic structure, such as pipe, a rail, a rolled metal product, a reservoir, a bridge, a vessel a cable, or electrical power transmission lines, is disclosed. The device includes a pulse generator being used to irradiate a part of the metallic structure, a sensor array registering a response from this part of the structure, and a GPS. The sensor array is located in proximity to the structure and measures its magnetic field gradient at a distance of up to 20 cm from the structure without any surface preparation treatment. A set of magnetic scanner sensors includes at least three sensors, positioned along the 3 orthogonal dimensions. An analogue-to-digital converter digitizing the sensor signal which is wirelessly transmitted to the calculation unit.

A calculation unit exploits an inverse magneto-strictive (Villari) effect of changing material's magnetic susceptibility under applied mechanical stress. Such changing results in gradient distribution of the magnetic field along the area of the structure that has a magnetic field anomaly. The distribution, in turn, reflects a presence and a value of the magnetic field anomaly at the given location. An absolute value of the mechanical stress, which corresponds to said anomaly, is further deducted, thus characterizing a mechanical defect of the structure, optionally using pre-determined information such as look-up tables, standards, thresholds, or an alternative contact measurement such as a contact probe.

The sensor array functions without removing the non-metallic cladding of the structure, such as a concrete wall around a metallic pipe, for example. The sensor array measurements can also be performed from inside the pipeline.

The device detects foreign objects that are present in vicinity of the structure, measuring relative distances and angles between themselves and the found anomaly. The discovered information is visualized by representing a topological map of the structure in real coordinates, showing simultaneously a structure layout, the foreign objects in vicinity, the location, and calculated three-dimensional values of the mechanical stress.

The device is also capable of measuring a natural Earth's background magnetic field without engaging the pulse generator. Such measurement is subtracted from the sensor signal to improve accuracy of the anomaly(s) location.

The device is operated by a battery with a residual charge indicator to ensure a quality and reliability of the identification in the field conditions and can perform without interruption of the structure's normal operation.

A method for discovering, identification, and monitoring of mechanical defects of various nature, causing the concentration of mechanical tension in metallic structures, is also disclosed. The method comprises irradiating a part of the metallic structure with electromagnetic pulses, performing mechanical stress measurement of the metallic structure by a sensor array placed in proximity to the structure and producing a digitized sensor signal and digitizing the sensor signal. The method also includes analyzing the digitized signal in a calculation unit using the inverse magneto-strictive effect providing information about the presence and the value of the magnetic field anomaly at the given location of the structure. The method calculates absolute values of the mechanical stress around the anomaly, thus unveiling and characterizing the mechanical defect of the structure.

BRIEF DESCRIPTION OF THE DRAWINGS

FIG. 5: A display unit of the magnetic tomography device according to the invention with a number of lights on a front panel. The display unit shows a stress-deformed state and a risk-factor of the at least one portion with the magnetic field anomaly.

FIG. 7A shows a diagram taken along the at least one portion of the ferromagnetic underground structure, with FIG. 7B showing the measurements along the same at least one portion of the ferromagnetic underground structure taken one year later.

DETAILED DESCRIPTION OF THE PREFERRED EMBODIMENT

The present invention describes the contact magnetic scanner device that uses a magnetic tomography (MT) for contact magnetographic identification and analysis of mechanical flaws/defects, optimized for extended metallic constructions inspection. The invention can be used in combination with a non-contact identification. The invention can be applied to a variety of extended metallic structures, such as a pipe, a rail, a rolled metal product, a reservoir, a bridge, a vessel, a cable, or electrical power transmission lines.

The use of MT devices has following advantages: 1) applicable for unpiggable pipelines or other objects where an in-line inspection method is inapplicable; 2) the objects to be inspected include but are not limited to: compressor stations pipelines, pipeline inclusions, water-supply pipelines in cities; 3) the use of MT devices doesn't require any preparation of the pipeline for testing such as cleaning, opening the pipe, or stopping pipeline operation; 4) the use of MT devices doesn't require magnetizing of the object's pipes; 5) an MT device is capable of detecting flaws of various types including long crack-like pipeline defects and welding defects; 6) the use of MT devices doesn't have a limitation on the structure diameter, configuration and protective coatings, for example, change of pipe diameter/wall-thickness, turns and their directions, transported product (e.g., gas, oil, or water), inside pressure, and pipeline protection (e.g., cathodic protection, etc).

The MT device is able to evaluate the degree of danger of defects by the level of concentration of mechanical tensions rather than defect geometry (e.g. length-width-depth) and is particularly suitable for running a database on condition certifications of objects of any length and any monitoring period.

The MT device implementation guarantees minimal customer resources use for monitoring preparation and repair work, such as: i) reduced work volume and total costs of pipe access work; ii) greatly reduced times for full diagnostic work—repair evaluation—repair planning—repair cycle; iii) provides pipe corrosion prognosis and estimates levels of tense-deformed state of the pipeline under current operating conditions.

The MT device application provides for remote metal flaws monitoring, which is particularly suitable for hidden ferromagnetic constructions of extended length.

Figure 1:
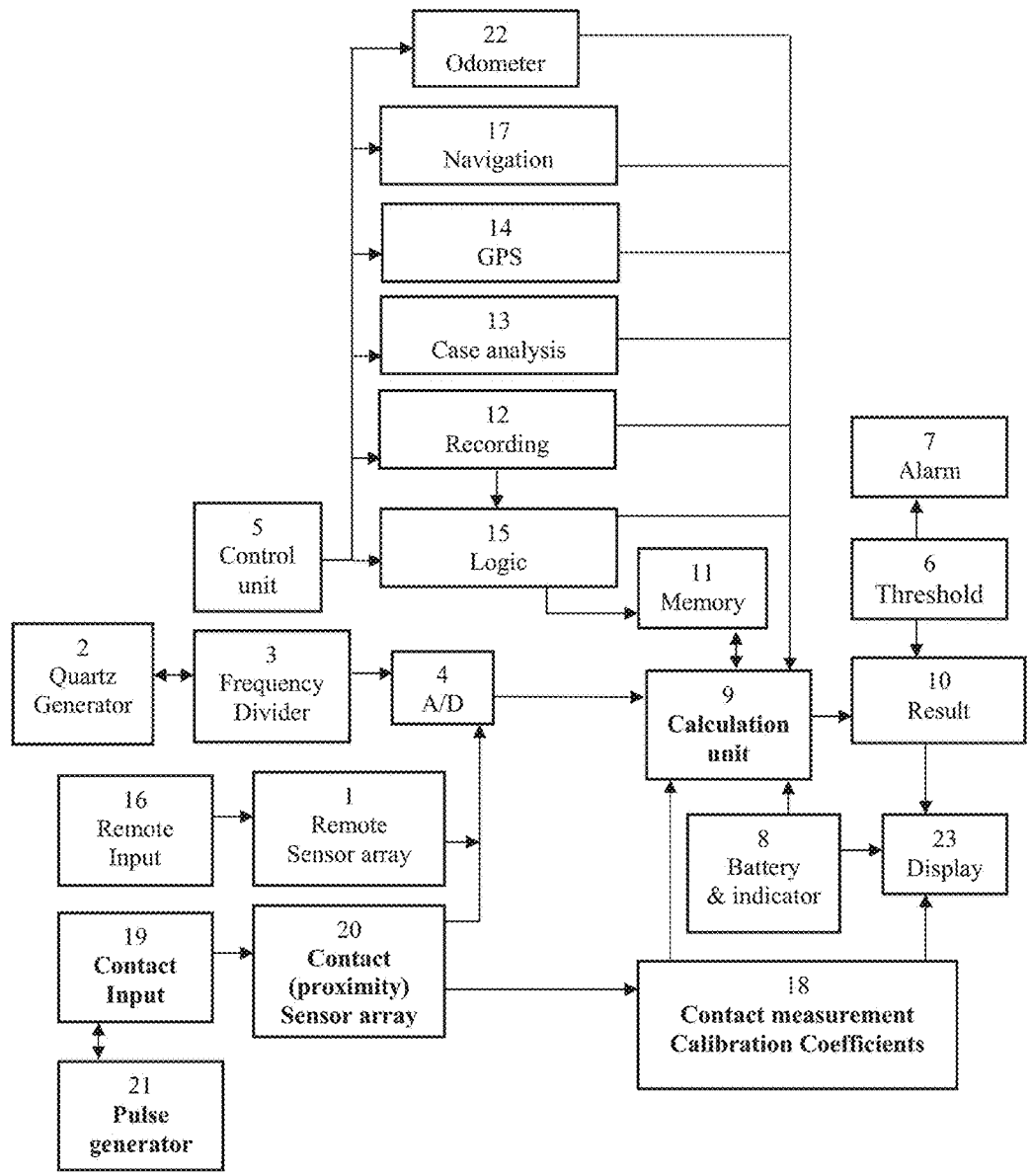
FIG. 1: The block-diagram of the device for discovering, identification, and monitoring of mechanical defects in metallic structures using a contact method, optionally, in combination with a non-contact technique.

The general combined block-diagram of the method is shown in FIG. 1.

The magnetic tomography device is based on using the inverse magneto-strictive (Villari) effect—i.e., the changing of the material magnetic susceptibility under applied mechanical stress. Generally, such technique uses "natural" magnetization of the ferrous pipes by the magnetic field of the Earth. The changing of magnetic susceptibility results in distribution of magnetic field gradient along the structure surface area under measurement, thus providing information about the presence and the value of the magnetic field anomaly at the given location of the structure.

The term "contact measurement," as used herein, is defined as the measurement being used from a small distance from the surface of the structure under testing. Preferably, such a distance is defined as a small distance if it is less than 5 cm from the surface of the structure. Furthermore, in the invention, applying an additional (pulsed) magnetic field is preferred.

The term "remote measurement," as used herein, is defined as the measurement being used from a substantial distance from the structure under testing. In contrast to the contact measurement (non-destructive or distractive), the remote sensor is not necessarily located in close proximity to the structure. Preferably, in the invention, the substantial distance has a value of 1-50 m, making the disclosed device especially effective for testing structures located deep underground or underwater.

The remote measurement is capable of identifying the anomalies by deviation of the Earth's magnetic field at each location from a background value, without applying an additional magnetic field during the measuring.

The contact measurement device is also capable of localizing coordinates of foreign objects in the vicinity of the structure and making a linkage between the anomalies' locations and the foreign objects' locations around the anomalies. Preferably, in the invention, the device finds coordinates of foreign objects which can be present in the vicinity of the structure and measures a distance/angle between those foreign objects and the structure's anomaly.

Both the remote and contact measurements are further capable of localizing coordinates of the structure and detecting anomalies with localized coordinates within the extended metallic structure based on measuring a value of the Earth's magnetic field at multiple locations in the vicinity of the structure.

The present invention discloses the Contact Magnetic Scanner—a device for the contact detection of the defects in metallic structures. The present invention effectively overcomes the aforementioned disadvantages of contact defect monitoring and detection.

Similar to the remote method, the contact method, at a given measurement point, the presence of the magnetic field anomaly and its magnitude (the local stress at the remote area) is determined based on a comparison between the increments (modules) of the Earth's magnetic field values (magnetic moments). Such a calculation method is based on a dipole approximation of the remote stress-concentrator. The solution of the problem of the magnetic moment calculation results from a system of algebraic equations, which, for example, is described in U.S. Pat. No. 4,309,659.

The disclosed device expands the scope of device applications for different types of metallic structures (e.g. confined extended, small and large), ii) provided real-time operational means by including data preprocessing and calibration, iii) increases the identification sensitivity of the defects located at the surface and within the volume of the object by including an additional pulse-magnetization unit, v) using a contact tomography technique in order to add 3D visualization capabilities using a 3D model of the tested object. The information visualization (display) unit of the device represents a topological map of the structure in real coordinates, showing simultaneously a structure layout, the foreign objects in the vicinity, the calculated values of a mechanical stress, and the location of the found anomalies.

The disclosed device uses pre-determined information for structure anomaly identification and localization. Such pre-determined information can be a look-up table, preset standards and thresholds, an alternative contact measurement, or a combination of the above.

Moreover, the device can combine a contact and non-contact measurement increasing the reliability and accuracy of information about the necessary repair or a stop alarm. It can be done using the risk-factor ranking tables based on the absolute values of stress, compared against the values from regulatory documentation (for a particular object).

Preferably, in the invention, the device performs the identification of anomalies without interruption of the structure's normal operation.

Increasing the efficiency of the method by applying a 3D visualization-assisted maintenance and repair schedule (with the real values of mechanical stress) to the actual structural layout, such as a pipeline integrated into the existing topology.

Such technological outcome can be achieved, mainly, due to the following innovative means: i) Contact (object surface) identification of the local defects and their respective risk-factors; ii) Comparing the remote measurement with measurements obtained locally; iii) Comparing the resulting measurements against the values from regulatory documentation (for a particular object); iii) Graphical 3D visualization of the obtained information using the actual topological layout of the area and the structure in absolute geographical coordinates.

Remote registration of magnetic field anomalies in extended metallic structures (such as a pipe) is performed in a predetermined coordinate system relative to the structure (axis) with a known (fixed) remote sensor array aperture. The coordinates of each single measurement along the structure can be chosen accordingly to the cross-section size and burial depth of the (underground, underwater) structure. It results in the matrix distribution of magnetic field gradient along the structure's surface area under each single measurement. The presence and the value of the magnetic field anomaly at the given location are derived from the comparison of different increments of the Earth's magnetic induction vector modulus.

Similar to the remote measurements, the contact measurement also includes a device to measure the magnetic field vector in Cartesian coordinates, by moving the registration device (magnetometer) along (above) the metallic structure (of arbitrary configuration, in general) and registration of the magnetic field anomalies. Such anomalies are calculated by a deviation from the background values (calculated using matrix transformations).

The contact device is also connected to the data recording unit and decoding system that provides conclusive information about the presence and location of the defects in the form of magnetograms that show the location of the defective pipe sections and their degrees of risk.

Similar to the remote measurements, the contact measurement of the extended object (such as pipeline) uses the recording of the magnetic field that is carried out in a pre-defined coordinate system at specifically defined measuring points by a set of sensors having a pre-selected aperture (base), K2. This aperture corresponds to the axis of the extended object with a measuring step, K1.

The exact location of measurement points is defined from the diameter and underground depth (e.g. of the pipeline), using coefficients K1, K2, and K3, where: K1 is the measuring step (registration of the magnetic field induction)=0.2 m, for example; where K2 is the aperture (the base) of the sensors, chosen from the ratio $0.7\ D \leq K2 \leq 1.4\ D$; where D is the diameter of the structure (pipeline), and where K3 is the depth of the pipeline, or the shortest distance from the metallic construction to the surface, in meters.

In the case of a non-linear (or small) extended object the contact registration of the magnetic field is carried out in a fixed coordinate system. In this case, registration is possible at different relative positions of the sensors and their arbitrary orientation with respect to the object (coplanar or collinear).

To verify the anomaly angular position along the structure (pipeline) circumference, the angular scanning step, K1, should not be larger than 30 degrees with the pre-defined distance between the sensors, K2, to ensure the required accuracy of calculations.

The block-diagram of such a device is shown in FIG. 1. With reference to FIG. 1, the device for contact and, optionally non-contact, measurements comprises a sensor array for remote measurements (1), a sensor array for proximity (contact) measurements (20), a quartz generator (2), a frequency divider (3), an analogue-to-digital converter (A/D) (4), a control unit (5), a threshold unit (6), a light- and sound-alarm unit (7), a battery with a charge indicator (8), a calculation unit (9), a (resulting) information unit (10) with a display unit (23), a non-volatile memory unit (11), a recording unit (12), a case-analysis unit (13), a pulse generation unit (21), an odometer unit (22), a GPS unit (14), a navigation unit (gyroscope/accelerometer) (17), and a logic unit (15). The device performs in the following manner:

The remote sensor array (1) registers induction gradients of the magnetic field (16) within the construction under testing.

The proximity sensor array (20) registers induction gradients of the magnetic field (19), the gradients corresponding to reflections of the EM pulses from the structure; the EM pulses being generated by the pulse generator (21). The signal from the proximity sensor is used as a calibrating measurement.

By using an A/D converter (4), both digitized signals (remote and contact) are: i) inputted into calculation unit as a preliminary data; ii) recorded by the memory unit (11). The Quartz generator (2) controls the frequency of the A/D converter (4).

The control unit (5) through the logic unit (15) controls the case analysis unit (13) with predetermined database and lookup tables, the recording unit (12), the GPS unit (14), the navigation unit (17) and the memory unit (11).

The calculation unit (9) receives the information from units (12), (13), (14), (17), (20), (22) through the memory unit (11), controlled by logic unit (15).

The real-time information from (4) is compared with the information from the threshold unit (6). By these means, the visualization of the real-time data against the threshold values is provided, enabling the alarming (by the unit (7)) of an operator about potentially dangerous operational conditions of the structure. The remaining charge of the battery (8) is monitored. The calculation unit (9) is responsible for the information processing, providing the information to the resulting and visualization unit (10).

The calculation unit (9) unit receives the digitized signal, uses the inverse magneto-strictive effect of changing of material magnetic susceptibility under applied mechanical stress resulting in gradient distribution of the magnetic field along an area of the structure that has a magnetic field anomaly, the distribution of magnetic field gradient providing an information about a presence and a value of the magnetic field anomaly at the given location of the structure and a mechanical stress, corresponding to the anomaly.

The calculation unit (9) further calculates absolute values of a mechanical stress around all found anomalies in the metallic structure using the measured values of the Earth's magnetic field for each anomaly and applying the calibration coefficient. As a result, the calculation unit is capable of identifying and localizing said signal anomalies.

The calculation unit may be located at a distance from the sensor array, and the digitized signal is transmitted to the calculation unit via a wireless connection.

The measured magnetic field values from 2 inputs (16) and (19), local stresses at the remote area are recorded at each measurement point, (both for contact and optional remote sensor, independently), then further compared with other measurements within a respective segment of the metallic construction. By these means, the anomalies (levels of stress-deformation) that deviate from the baseline magnetic field values are selected. Thus, the location of each stress-related deformation is derived from the maximum concentration value of the magnetic field after comparing it with the previous measurements.

The visualization unit has a 3-dimensional display means (23) in order to provide a 3-D representation of the density of magnetic field strength distribution, found defects and its risk-factors along with the topological (3D) map of the structure under testing.

The resulting and visualization unit (10) also accommodates inputs from the threshold unit (6) and the light-/sound-alarm unit (7) which enables identification of the parameters' deviation from the background level, as well as (e.g., wirelessly) informing an operator about the deviation value in real-time, respectively.

Moreover, the resulting and visualization unit (10) is capable of comparing the remote signals (16) with in-contact measurement (19) and producing a set of calibration coefficients in order to calibrate the resulting calculated data of found magnetic anomalies.

The situational case-analysis unit (13) enables the analysis of the information in the context of pre-determined technological information and schemes, which, in combination with the GPS unit (14), provides for more accurate topological mapping.

In the preferable configuration of the device, a GPS sensor (14) is complemented by a navigation unit that includes gyroscope(s) and/or a set of accelerometer(s) (17), and odometer unit (22) enabling the recording of the device's angle-positioning relative to the extended metallic structure cross-section at each moment of the magneto-graphical measurements. The recorded angle-positioning data (including positioning relative to horizon) is used further to correct the magneto-graphical measurements due to structural bending/turning-related deviations.

Accordingly, the absolute coordinates of discovered defects relative to the (visible) reference objects can be obtained with the following registration in the database during the equipment assessment report.

In the preferable configuration of the mentioned device, each sensor array, (1) and (20), consist of a few 3-compenent arrays, positioned along the 3 orthogonal dimensions. Alternatively, each array includes a few single-component sensors, such as optically pumped quantum analyzers. Using the optically pumped quantum analyzers in the sensor array (1) allows for higher flaw-detection accuracy in underground constructions, well-suited for detecting relatively small values of mechanical stress, and/or deeper underground installation.

Since the sensor array (1) and (20) can be rotated above the surface of the structure during the scanning procedure, it is possible to implement a polar coordinate system for the detection of defects, in combination with the data from the gyroscope/accelerometer unit (17).

The recording process is arranged in a discrete manner, enabling an independent storage and access for different recorded portions (memory segments) of the scanning.

In the preferable configuration of the disclosed device, the unit (9) calculates: i) magnetic field gradients distributed along the square area within the defined segment of the structure, ii) the values of the local mechanical stress within the defined segment of the structure.

The device allows for identifying the location of defects using both in-contact and remote magnetic measurements.

Moreover, it expresses the calculations in real-time, also providing the visualization of the information in the form of tomograms with reference to the 3D model of the controlled object.

Moreover, the device provides automated evaluation of the defects risk factor at respective identified locations, allows automatic processing, interpretation, and archiving of non-destructive testing results.

In an alternative configuration of the disclosure, the calculation unit (9) can be realized similarly to that in U.S. Pat. No. 4,309,659.

Moreover, in an alternative configuration of the present invention, the recording unit (12) can be realized similarly to that in Patent No. RU 2037888.

Figure 2A:
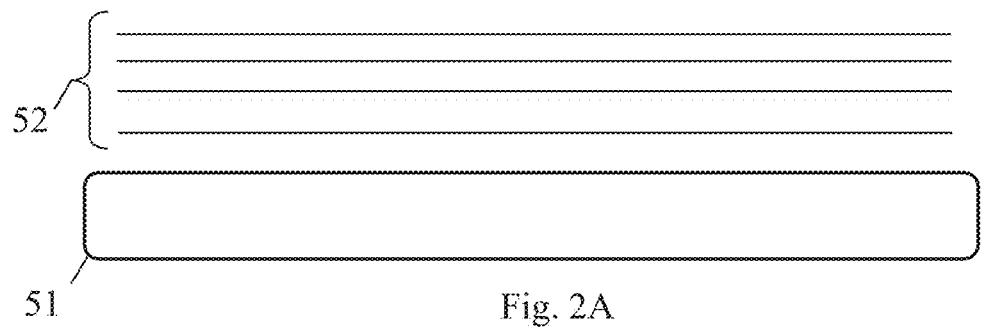
FIG. 2A-2C: A general principle of operation of the contact and non-contact magneto-graphic techniques used in metallic structure defects monitoring and integrity assessment.
Figure 2B:
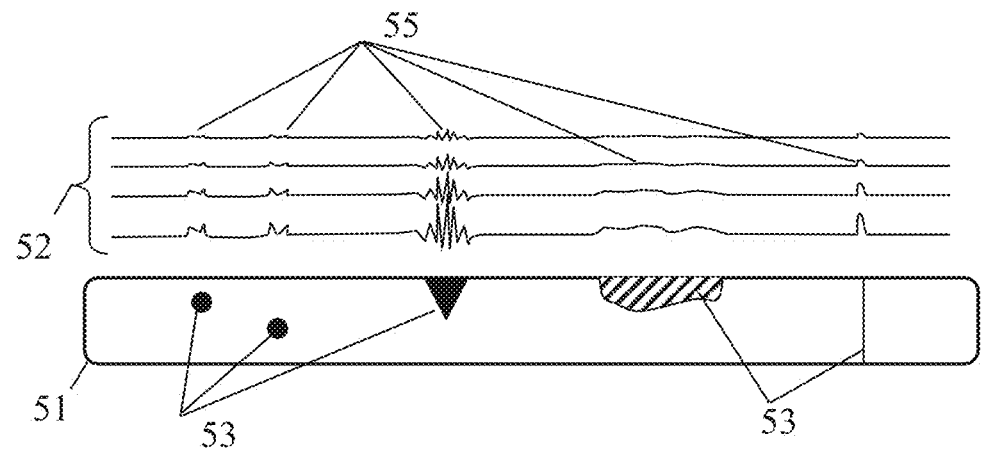
Figure 2C:
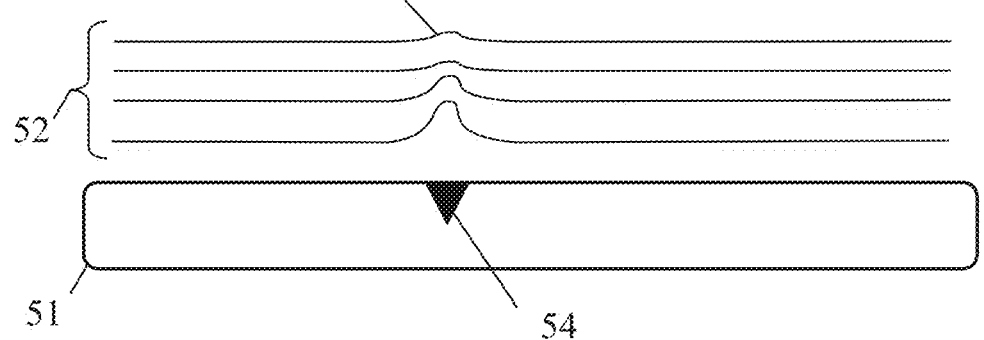

The principle of operation of the device shown in FIG. 1 is explained further in FIG. 2. FIG. 2A shows the structure (51) without defects, with the preliminary magnetic tomography charts (magnetogram) (52) showing the measured background (calibrated to zero) level of magnetization. FIG. 2B shows the same structure (51) with the potential defects (53), (54) corresponding to the deviations of the tomography charts (55). FIG. 2C shows the same structure (51) with the processed tomography charts (55), showing the location of the defect (54) that requires immediate attention (unacceptable, pre-alarm technical condition, alarm), based on the local mechanical stress value estimate.

As mentioned before, the magnetogram (52) attributes and characterizes the section of the structure by registering and analyzing changes in the magnetic field of the structure such as pipeline. These changes are related to stress, which, in turn, is related to defects in the metal and insulation. Magnetic measurements data is collected from the surface and includes the detected anomalies. Such detected anomalies are functions of a local stress and/or local mechanical tension and structural changes in the metal. Moreover, a post-processing of this experimental data enables the visualization of the flaws in the structure.

The device can operate on a metallic structure which is covered by a non-metallic cladding and the sensor array performs the measurement without removing the cladding, for example, when the metallic structure is a pipeline and the cladding is a pipeline insulation cover. Moreover, the device (sensor array) is capable of performing measurements from inside the structure, such as a pipeline.

The described MT device does not measure the dimensions of geometric defects alone, but, instead, provides a stress measurement caused by these defects and identifies their character, location, and orientation in accordance with the location and orientation of the area of stress. Linear and angular coordinates of flaws in the metal and coating have been experimentally defined within a tolerance of +/−0.25 m.

The device explained by FIG. 1 and FIG. 2 can effectively identify and analyze the magnetic field anomalies in areas with stress concentrators caused by: i) defects or changes in structural conditions (such as metal loss, cracks, dents, lamination and inclusions); ii) erosion, seismic activity, or third-party damage.

Figure 3:
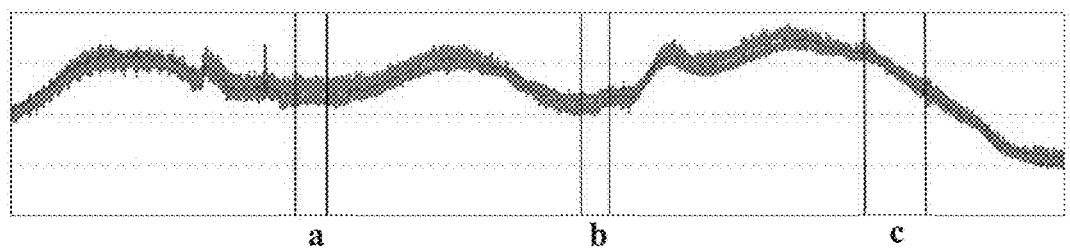
FIG. 3: An example of a single magneto-graphic measurement. The diagram represents the three areas of magnetic field anomalies (a), (b), and (c), corresponding to the respective local mechanical stresses. The area, (c), shows the evidence of the metal stress yielding-limit crossing.

FIG. 3 shows an example of a single magneto-graphic measurement. The diagram represents the three areas of magnetic field anomalies, (a), (b), and (c), corresponding to the respective local mechanical stresses. The area (c) shows the evidence of the metal stress yielding-limit crossing.

In parallel, the in-contact (proximity) defectoscopy has been performed at the location (c). The actual dimensions of defects (cracks and corrosion) have been evaluated. The magnetographic device calibration has been performed based on a difference between the measured signal (versus background) and the actual parameters of the defect(s) found. Then, the calibrated values of the anomalies have been used as a criterion. For this particular case, the calibrated values appeared to be 3-10 times higher compared to the background signal value. The follow-up magnetographic measurements have been performed in a real-time.

The presented MT device helps to plan necessary structural maintenance procedures and define their priorities. The device is particularly efficient when the magneto-graphic material (Magnetic Tomography) inspection is applied to extended metallic constructions, revealing its flaws against the topological map of the structure.

Moreover, the device enables direct monitoring of the defective construction segments with still acceptable technical conditions. It allows a long-term database support for the follow up monitoring, certification, prognosis, and operational timeline for the structure.

Preferably in the invention, the non-destructive detection of anomalies in the structure is performed using a magnetographic technique such as MT.

The goals of the present invention are: i) to increase the method's applicability area; ii) to increase the accuracy of the priority scheduling for required maintenance and repair procedures; iii) to broaden the spectrum of the potentially scheduled repair procedures, based on the additional data.

In one embodiment of the invention, a magnetic scanner portable device is moved by a service person above and along a ferromagnetic underground or underwater structure to monitor and assess the underground structure in a potentially unstable zone of the Earth's crust. Each inspection is being conducted at a given time of the year to collect data about a current status of the ferromagnetic underground structure. This information is processed, displayed, and stored. A goal of the inspection is to identify at least one portion of the underground or underwater structure with a magnetic field anomaly. The magnetic scanner portable device can include at least one set of magnetic scanner sensors, where each set has at least three sensors.

In another embodiment of the invention, at least one set of permanent magnetic scanner sensors is provided in a vicinity of an underground structure to perform a long term monitoring of the underground structure's integrity. The underground structure, which could be, for example, a pipeline, requires an integrity management. Integrity management is a general term, given to all efforts including but not limited to the structure design, construction, operation, maintenance, etc. While a major cause of underground structure failures is corrosion, another cause is external interference. Those underground structures located in seismically unstable areas are particularly prone to failures caused by movement of geological formations.

But even if the underground structure of interest (for example, a pipeline) is placed in a seismically stable area, this structure will be effected by incremental changes in the surrounding geological formations, which will eventually lead to an underground structure catastrophic failure. Furthermore, another cause of gradual degradation of the underground structure leading to a catastrophic failure is human activity in areas adjacent to the structure. Such human activities include but are not limited to construction, especially large scale construction activities, irrigation efforts, gas and oil exploration, etc. Shock wave propagation, especially in heavy/solid layers of the geological formations, and even through the underground structure itself, makes certain structures vulnerable to human activities taking place far away from a location of the structure.

Given a high cost of repair for any kind of underground structure, this invention offers an opportunity to significantly reduce maintenance costs by predicting a catastrophic failure of an underground structure.

Prediction of catastrophic failure requires a long-term monitoring of the underground structure, which is accomplished through an array of permanent magnetic scanner sensors distributed on a terrain in a vicinity of the underground ferromagnetic structure. In this embodiment of the invention, the sensor array is placed in proximity along the structure and measures its magnetic field gradient at a distance from the structure. The array of sensors can also be placed in contact with the ferromagnetic underground structure. The sensor array can include at least one set of permanent magnetic scanner sensors, where each set has at least three sensors. The sensor array can also include at least two sets of permanent magnetic scanner sensors, where each set has at least three sensors.

Figure 4:
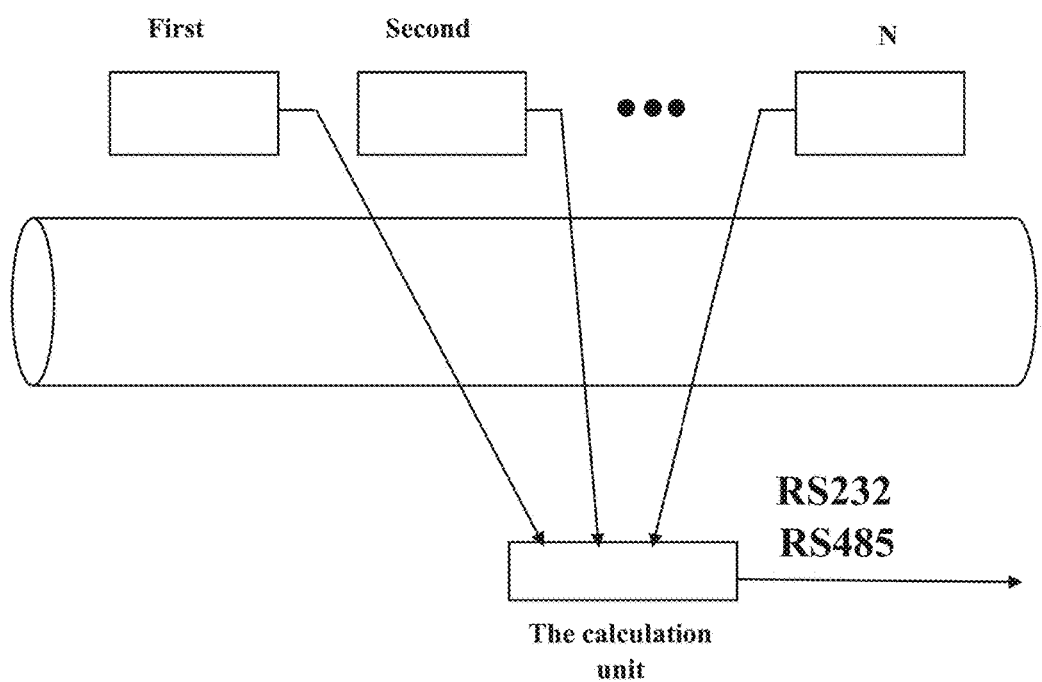
FIG. 4: An example of sets of permanent magnetic scanner sensors placed along at least one portion of the ferromagnetic underground structure (a pipeline) to monitor for a magnetic field anomaly.

FIG. 4 shows 1S; 2S . . . NS set of permanent magnetic scanner sensors, placed adjacent to the at least one portion of the underground structure (a pipeline) with the magnetic field anomaly. The 1S; 2S . . . NS sets of permanent magnetic scanner sensors can be encased in watertight packaging. The 1S; 2S . . . NS sets are coupled to a calculation unit 9, which collects and processes data from the at least one set of permanent magnetic scanner sensors 1S, 2S . . . NS. The sets 1S; 2S . . . NS can be coupled to the calculation unit 9 wirelessly. An interface between the at least one set of permanent magnetic scanner sensors can be a digital interface, where the data from the at least one set of permanent magnetic scanner sensors is provided to the calculation unit 9 at a discrete time with an interval of no more than, for example, about one hour.

The calculation unit 9 is connected to the display unit 23. FIG. 5 shows the display unit 23 according to the invention with a number of lights on a front panel. The display unit 23 can be configured to show a stress-deformed state (SDS) and a risk-factor (RF) of the at least one portion with the underground structure with a magnetic field anomaly. A magnetic field anomaly, presented by SDS and RF, at the at least one portion of the structure can be displayed in color coding (red, yellow, and green) to indicate a status of the portion. A more sophisticated display system can be used if a necessity arises, for example, in a case of a complex structure.

Figure 6:
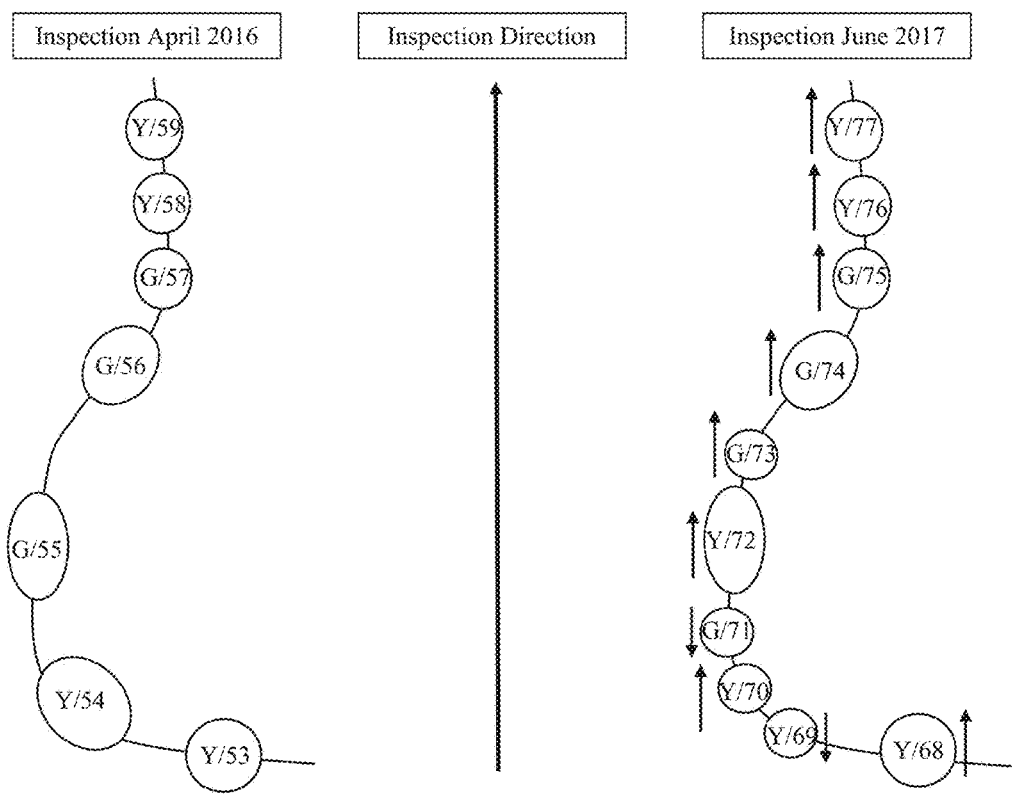
FIG. 6: Examples of inspections of the at least one portion of the ferromagnetic underground structure made one year apart.
Figure 7A:
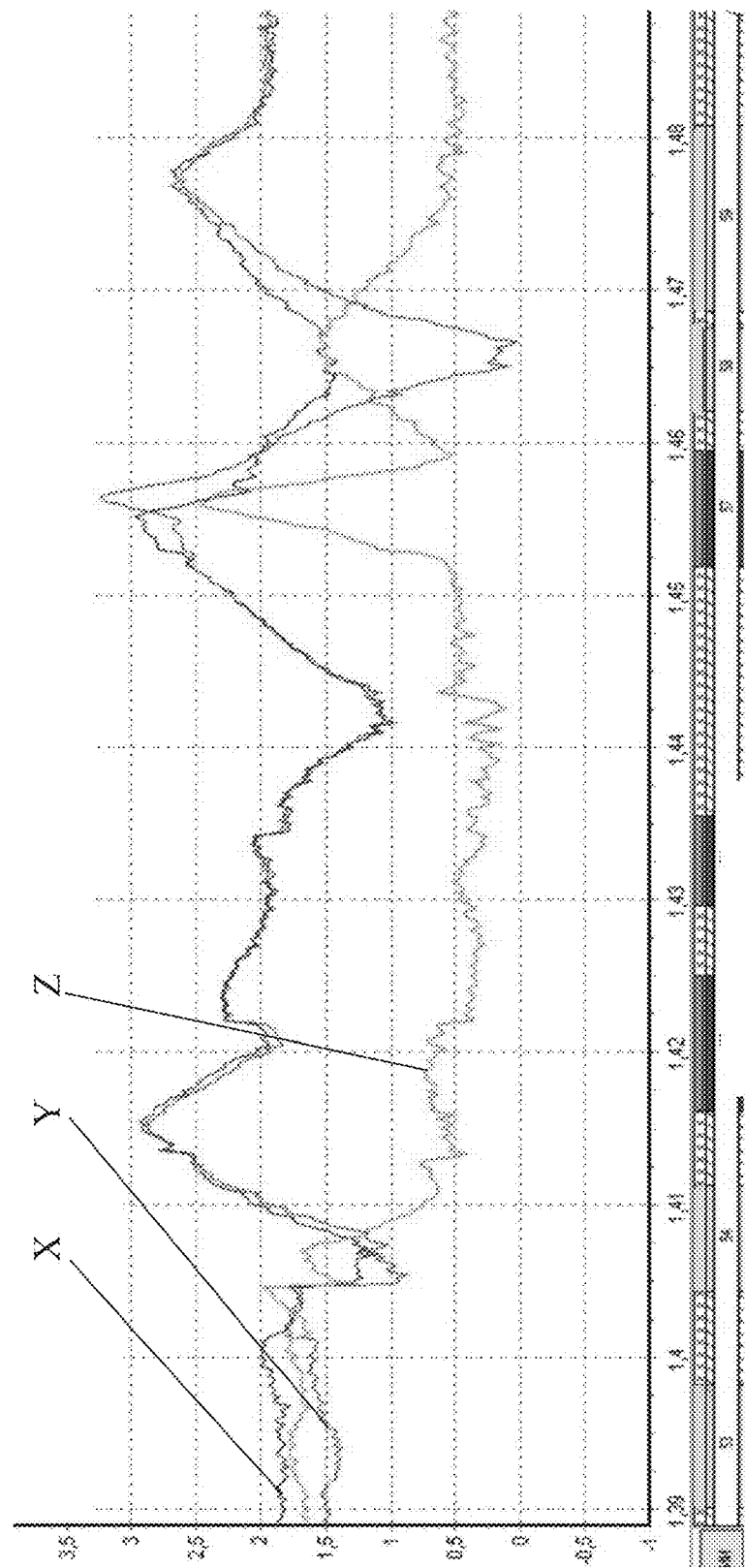
FIG. 7A-7B: An example of magneto-graphic measurements taken by a set of three, X, Y and Z, magnetic scanner sensors.
Figure 7B:
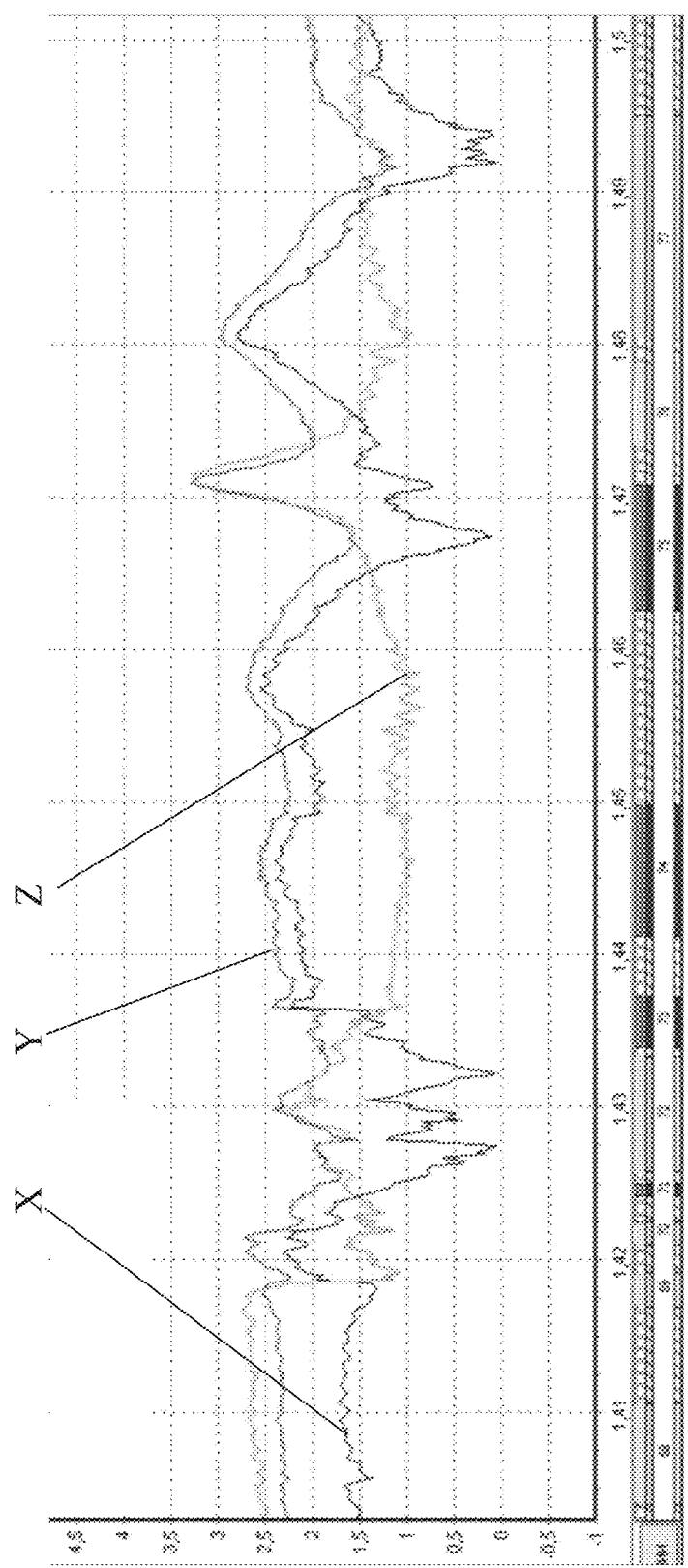

FIG. 6 shows magnetic field anomalies 53-59 along the underground structure, detected during an inspection, and magnetic field anomalies 68-77, confirmed during another inspection a year later along the same ferromagnetic underground structure. FIG. 7A is an example of magneto-graphic measurements taken by a set of three, X, Y, and Z, magnetic scanner sensors along a portion of the ferromagnetic underground structure with the anomalies 53-59. FIG. 7B shows the measurements along the same portion of the ferromagnetic underground structure taken one year later. These measurements revealed the anomalies 68-77 as shown in FIG. 6.

Another embodiment of the invention uses fewer sets of permanent magnetic scanner sensors than in the embodiment discussed above. This is a way to reduce the cost of long-term monitoring by placing sensors only in strategically important portions of the structure or next to those portions, which were flagged as potentially vulnerable. Consequently, the total number of sensors in the array can be significantly reduced. This is especially true when the structure of interest is deep underwater, and the cost of watertight sensors and their installation is high.

Yet another embodiment of the invention is directed to the method for discovering, identification, and monitoring of mechanical defects in a ferromagnetic underground or underwater structure. The method provides at least one magnetic scanner portable device to inspect at least one portion of the ferromagnetic underground structure. The underground structure is inspected using the at least one magnetic scanner portable device to identify at least one portion with a magnetic field anomaly.

The method further provides for at least one set of permanent magnetic scanner sensors to monitor the at least one portion with the magnetic field anomaly, revealed by the inspection. The at least one set of permanent magnetic scanner sensors is placed adjacent to the at least one portion with the magnetic field anomaly. The at least one set of permanent magnetic scanner sensors is coupled to a calculation unit.

The calculation unit collects and processes data provided by the at least one set of permanent magnetic scanner sensors. Further, the calculation unit displays on a display, which is coupled to the calculation unit, a stress-deformed state (SDS) and a risk-factor (RF) of the at least one portion with the magnetic field anomaly.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for discovering, identification, and monitoring of mechanical defects in a ferromagnetic underground or underwater structure, comprising:
    providing at least one portable magnetic scanner device;
    providing a ferromagnetic structure having at least one portion;
    inspecting the ferromagnetic structure to identify at least one portion with a magnetic field anomaly, wherein the underground structure is first inspected using the at least one portable magnetic scanner device;
    providing at least one set of additional permanent magnetic sensors to subsequently monitor the at least one portion with the magnetic field anomaly;
    placing the at least one set of permanent magnetic sensors adjacent to the at least one portion with the magnetic field anomaly, wherein the at least one set of permanent magnetic sensors is coupled to a calculation unit;
    collecting data provided by the at least one set of permanent magnetic sensors;
    processing the data with the calculation unit; and
    displaying on a display unit a stress-deformed state and a risk-factor of the stress-deformed state according to a material tension concentration of the at least one portion with the magnetic field anomaly,
    wherein the display unit is coupled to the calculation unit.

2. The method of claim 1, wherein sensors of the at least one set of additional permanent magnetic sensors are placed in a watertight packaging.

3. The method of claim 1, wherein the at least one set of additional permanent magnetic sensors is coupled to the calculation unit wirelessly.

4. The method of claim 1, wherein the at least one set of additional permanent magnetic sensors provide data for the calculation unit at a discrete time with an interval of no more than about one hour.

5. The method of claim 1, wherein the display unit comprises lights on a front panel, the display unit being configured to display a stress-deformed state (SDS) and a risk-factor (RF) of the at least one portion with the magnetic field anomaly.

6. The method of claim 1, comprising at least two sets of additional permanent magnetic sensors, each set including at least three sensors.

7. The method of claim 1, wherein the at least one portable magnetic scanner device includes at least three sensors.

8. The method of claim 1, wherein the at least one set of additional permanent magnetic sensors is placed in contact with the at least one portion with the magnetic field anomaly.

9. The method of claim 1, wherein the at least one set of additional permanent magnetic sensors is separated by a gap from the at least one portion with the magnetic field anomaly.

10. The method of claim 9, wherein the gap is less than about 50 meters.

11. The method of claim 9, wherein the gap is less than about 20 cm.

12. The method of claim 1, further comprising comparing signals from the at least one portable magnetic scanner device with signals from the at least one set of additional permanent magnetic sensors to produce a set of calibration coefficients.

13. The method of claim 1, wherein said display unit provides a 3-D representation of a density of magnetic field strength distribution, found defects, and said risk-factors, together with a topological 3-D map of the structure.

* * * * *